US010610383B2

(12) United States Patent
Pelisson et al.

(10) Patent No.: US 10,610,383 B2
(45) Date of Patent: Apr. 7, 2020

(54) PROSTHETIC KNEE JOINT FOR AN ABOVE-THE-KNEE AMPUTEE

(71) Applicants: COMMISSARIAT À L'ENERGIE ATOMIQUE ET AUX ENERGIES ALTERNATIVES, Paris (FR); CHABLOZ COMPOSANTS, Seyssinet-Pariset (FR)

(72) Inventors: Roland Pelisson, La Terrasse (FR); Pierre Chabloz, Saint Georges de Commiers (FR)

(73) Assignees: COMMISSARIAT À L'ENERGIE ATOMIQUE ET AUX, Paris (FR); CHABLOZ COMPOSANTS, Seyssinet-Pariset (FR)

( * ) Notice: Subject to any disclaimer, the term of this patent is extended or adjusted under 35 U.S.C. 154(b) by 52 days.

(21) Appl. No.: 15/483,426

(22) Filed: Apr. 10, 2017

(65) Prior Publication Data

US 2017/0290683 A1    Oct. 12, 2017

(30) Foreign Application Priority Data

Apr. 8, 2016 (FR) ...................................... 16 53120

(51) Int. Cl.
*A61F 2/64* (2006.01)
*A61F 2/76* (2006.01)
(Continued)

(52) U.S. Cl.
CPC .................. *A61F 2/64* (2013.01); *A61F 2/76* (2013.01); *A61F 2002/689* (2013.01);
(Continued)

(58) Field of Classification Search
CPC ........ A61F 2002/689; A61F 2002/6827; A61F 2002/6854; A61F 2/64
See application file for complete search history.

(56) References Cited

U.S. PATENT DOCUMENTS 1,994,185 A  *  3/1935  Alterman .................. A61F 2/64
                                                        623/30
3,405,219 A  *  10/1968  Sivet ...................... H05B 7/109
                                                        314/10

(Continued)

FOREIGN PATENT DOCUMENTS

FR       2464702 A1    3/1981
WO    2008080232 A1    7/2008

*Primary Examiner* — Christie L Bahena
(74) *Attorney, Agent, or Firm* — Oliff PLC

(57) ABSTRACT

Prosthetic knee joint includes: proximal part mobile in rotation around first axis between extended position and flexion position of prosthetic knee joint; the proximal part being mobile in first direction of rotation from extended position to flexion position, at least one part that is fixed when proximal part is moved in first direction of rotation; link part, arranged to connect the proximal part and part, and presenting contact surface with part; the link part and part being arranged so, when proximal part is moved in first direction of rotation, link part slides on contact surface being subjected to first friction force, when proximal part is moved in second direction of rotation, the link part slides on contact surface being subjected to second friction force strictly lower than first friction force.

25 Claims, 6 Drawing Sheets

(51) Int. Cl.
  *A61F 2/68* (2006.01)
  *A61F 2/70* (2006.01)
(52) U.S. Cl.
  CPC ... *A61F 2002/701* (2013.01); *A61F 2002/764* (2013.01); *A61F 2002/7635* (2013.01)

(56) References Cited

U.S. PATENT DOCUMENTS

| | | | |
|---|---|---|---|
| 3,599,245 A | 8/1971 | Blatchford | |
| 4,351,070 A | 9/1982 | Blatchford | |
| 6,673,117 B1 * | 1/2004 | Soss | A61F 2/64 623/24 |
| 2012/0283845 A1 * | 11/2012 | Herr | A61F 2/66 623/24 |
| 2016/0346156 A1 * | 12/2016 | Walsh | A63B 21/4009 |
| 2017/0151070 A1 * | 6/2017 | Sun | A61B 5/112 |

* cited by examiner

PROSTHETIC KNEE JOINT FOR AN ABOVE-THE-KNEE AMPUTEE

BACKGROUND OF THE INVENTION

The invention relates to the technical field of prosthetic knee joints for an above-the-knee amputee. The invention finds its application in particular in geriatrics.

STATE OF THE ART

A known prosthetic knee joint of the state of the art, of the lockable knee joint type, comprises:
- an articulation mobile in rotation around an axis perpendicular to a sagittal plane of the amputee between an extended position and a flexion position of the prosthetic knee joint;
- a locking mechanism of the articulation in the extended position when the amputee moves from a seated position to a standing position.

The locking mechanism is conventionally controlled by a cable enabling the articulation to be unlocked, i.e. the articulation to be released from the extended position, when the amputee wants to move from a standing position to a seated position.

Such a lockable prosthetic knee joint is not entirely satisfactory. One major drawback is in fact the abrupt unlocking of the articulation when the amputee wants to sit down. An elderly amputee, who is not too alert, is then liable to lose his balance. The elderly amputee is apprehensive of this situation and is therefore none too inclined to use this prosthetic knee joint regularly.

An object of the invention is therefore to propose a prosthetic knee joint that is reassuring for an elderly amputee, and is inexpensive in order to be taken care of by a health organisation such as the public health insurance body in France.

SUMMARY OF THE INVENTION

For this purpose, the object of the invention is to provide a prosthetic knee joint for an above-the-knee amputee, comprising:
- a proximal part designed to be connected to a prosthetic socket, the proximal part being mobile in rotation around a first axis perpendicular to a sagittal plane of the amputee between an extended position and a flexion position of the prosthetic knee joint; the proximal part being mobile in a first direction of rotation from the extended position to the flexion position, and mobile in an opposite second direction of rotation from the flexion position to the extended position;
- at least one part, the part being fixed when the proximal part is moved in the first direction of rotation;
- a link part, arranged to connect the proximal part and the part, the link part presenting a contact surface with the part; the link part and the part being arranged so that,
  - when the proximal part is moved in the first direction of rotation, the link part slides on the contact surface being subjected to a first friction force,
  - when the proximal part is moved in the second direction of rotation, the link part slides on the contact surface being subjected to a second friction force strictly lower than the first friction force.

Definitions

What is meant by "proximal" is the part which is situated closest to the residual member of the above-the-knee amputee.

What is meant by "distal" is the part which is farthest from the residual member.

What is meant by "sagittal plane" is a plane parallel to the median sagittal plane of the amputee.

When an elderly amputee wants to move from the standing position to a seated position, the prosthetic knee joint according to the invention performs a flexion resulting in rotational movement of the proximal part in the first direction of rotation. Sliding with friction of the link part slows down the movement from the standing position to the seated position. This slowing-down of the flexion of the prosthetic knee joint reassures the elderly amputee who can easily keep his balance until he has reached the seated position. A "braking effect" on flexion can be referred to. This slowing-down of the flexion of the prosthetic knee joint is also beneficial when the amputee wants to move from a seated position to a standing position stopping in at least one intermediate position in order to assist himself for example first of all by means of arm rests, and then with a walking stick or crutches. In the intermediate position or positions, placing of the amputee's weight back on the prosthetic knee joint is then accompanied by the "braking effect" which reassures the amputee.

The fact that the second friction force is strictly lower than the first friction force further facilitates moving from a seated position to a standing position compared with moving from the standing position to the seated position. This therefore encourages the elderly amputee to get up and move about.

Furthermore, the prosthetic knee joint according to the invention is inexpensive as slowing-down of the flexion is obtained by simple friction, not requiring any complex system such as a hydraulic jack.

The prosthetic knee joint according to the invention can comprise one or more of the following features.

According to one feature of the invention, the first and second friction forces, respectively noted $f_1$ and $f_2$, present a ratio $f_1/f_2$ higher than or equal to 10.

In this way, one advantage procured by such a ratio is to allow movement from a seated position to the standing position as easily as possible offering the less possible resistance for the amputee, while at the same time keeping a satisfactory slowing-down of the flexion of the prosthetic knee joint from the standing position to a seated position, or from a seated position to an intermediate position with the amputee's weight again being placed on the prosthetic knee joint.

According to one feature of the invention, the part is mobile when the proximal part is moved in the second direction of rotation.

In this way, one procured advantage is to overcome the resistance of the part when moving from a seated position to the standing position. It is therefore possible to obtain a ratio $f_1/f_2$ much higher than 10, for example of about 20.

According to one feature of the invention, the prosthetic knee joint comprises tensioning means arranged to exert a mechanical tension on the link part.

In this way, one procured advantage is the possibility to adjust the first friction force, and thereby the slowing-down of the flexion of the prosthetic knee joint, when the link part is flexible. An increase (respectively a decrease) of the mechanical tension exerted on the link part enables a higher (respectively lower) flexural strength to be generated.

According to one feature of the invention, the prosthetic knee joint comprises control means configured to control the tensioning means.

In this way, one procured advantage is the possibility of envisaging adjustment of the mechanical tension exerted on the link part during flexion of the prosthetic knee joint.

According to one feature of the invention, the tensioning means comprise a rotary tensioner, and the control means comprise a servomotor configured to modify a torque exerted on the rotary tensioner.

In this way, one advantage procured by the rotary tensioner is to limit the wear of the link part (for example compared with a clamp surrounding the link part to grip the latter), in particular when the link part is a cord.

According to the shock of the invention, the prosthetic knee joint comprises a stress gauge arranged to measure the torque exerted on the rotary tensioner.

In this way, one procured advantage is to know the torque in order to adjust it by means of the control means.

According to one feature of the invention, the proximal part presents a pivoting angle between the extended position and the flexion position in a sagittal plane of the amputee; the prosthetic knee joint comprising measuring means arranged to measure the pivoting angle, the measuring means preferably being selected from the group comprising an accelerometer, a gyrometer, or a potentiometric sensor.

In this way, one procured advantage is the possibility of adjusting the mechanical tension exerted on the link part during flexion of the prosthetic knee joint according to the pivoting angle.

According to one feature of the invention, the prosthetic knee joint comprises a force sensor arranged to measure the force exerted by the link part on the part.

According to one feature of the invention, the prosthetic knee joint comprises warning means configured to warn the amputee as soon as the force measured by the force sensor exceeds a threshold, the warning means preferably comprising a vibrator.

In this way, one procured advantage is to give the amputee the possibility of anticipating the beginning of the flexion phase of the prosthetic knee joint.

According to one feature of the invention, the prosthetic knee joint comprises flexible biasing means to bias the proximal part to the extended position.

In this way, one procured advantage is to facilitate movement from a seated position to the standing position.

According to one feature of the invention, the link part is selected from the group comprising a strap, a cord, or a belt.

In this way, the procured advantages are the simplicity and reduced cost of such link parts.

According to one feature of the invention, the link part comprises a part wound around the part, the wound part preferably being a cord.

In this case, one advantage procured by the cord is to reduce the volume in significant manner, for example compared with a strap, by winding it around the part with a plurality of winds.

According to one feature of the invention, the prosthetic knee joint comprises a set of parts, the parts of the set being fixed when the proximal part is moved in the first direction of rotation; the link part being arranged to connect the proximal part and the set of parts, the link part presenting contact surfaces with the set of parts; the link part and the set of parts being arranged in such a way that, when the proximal part is moved in the first direction of rotation, the link part slides on each contact surface being subjected to the corresponding first friction force.

In this way, a procured advantage is to increase the total friction force to which the link part is subjected by increasing the number of fixed parts when the proximal part is moved in the first direction of rotation, which enables flexion of the prosthetic knee joint to be slowed down even further.

According to one feature of the invention, the link part and the set of parts are arranged so that the link part forms strings around the set of parts.

In this way, one advantage procured by this zigzag geometric configuration (i.e. the strings describe a winding line presenting curves alternately directed in the opposite direction) of the link part relatively to the set of parts is to increase the total friction force to which the link part is subjected, while at the same time preserving a satisfactory compactness of the prosthetic knee joint.

According to one feature of the invention, the prosthetic knee joint comprises:
   a distal part, designed to be connected to a prosthetic foot, the distal part being mobile in rotation around a second axis perpendicular to a sagittal plane of the amputee between a forward movement position and a backward movement position of the prosthetic foot; the distal part being mobile in a first direction of rotation from the forward movement position to the backward movement position;
   an additional link part of arranged to connect the proximal part and the distal part so that, when the proximal part is moved in the first direction of rotation, the distal part is moved in the first direction of rotation.

In this way, one procured advantage is to move the prosthetic knee joint to the front of the amputee when the latter moves from a standing position to a seated position. This frontward movement of the prosthetic knee joint during the flexion substantially improves the stability of the amputee no longer has to incline his chest to the front. Indeed, under conditions of use, the prosthetic foot is fixed, being kept on the ground by the weight of the amputee. Consequently, the rotational movement of the distal part in the first direction of rotation results in a forward movement of the proximal part, and therefore of the prosthetic knee joint.

According to one feature of the invention, the additional link part and the set of parts are arranged so that the additional link part forms strings around the set of parts.

In this way, one procured advantage is that additional safety is obtained when the amputee is walking. When the heel of the prosthetic foot is placed on the ground, the extended position is further maintained by frictions of the additional part which stretches in contact around the set of parts. In other words, when the person is walking, placing the heel on the ground stretches the additional link part which, on account of the strings, is subjected to an amplified friction which blocks the prosthetic knee joint in the extended position, which is particularly advantageous in the absence of control electronics. On the other hand, when the person stops and is pressing on the toe of the prosthetic foot, the additional link part is not subjected to any significant friction force. Only the link part is subjected to a friction force enabling slowing-down of the flexion of the prosthetic knee joint to be obtained.

According to one feature the invention, the additional link part is selected from the group comprising a strap, a cord, or a belt.

In this way, the procured advantages are the simplicity and reduced cost of such additional link parts.

According to one feature of the invention, the proximal part and the distal part present speeds of rotation in the first direction of rotation respectively noted $Vp_1$ and $Vd_1$; the prosthetic knee joint comprising suitable means for receiving the additional link part, the means being configured in such a way that $Vd_1$ is strictly lower than $Vp_1$ with preferably $Vp_1/Vd_1 \geq 3$.

In this way, one procured advantage is to obtain, by gearing-down, a large movement of the proximal part (and thereby of the prosthetic knee joint) in the frontward direction of the amputee when the latter moves from the standing position to a seated position, while at the same time preserving a satisfactory compactness of the distal part.

According to one feature of the invention, the proximal part presents an oblong shape in a sagittal plane of the amputee.

In this way, one advantage procured by the oblong shape (i.e. longer than it is wide) is to obtain a movement of the proximal part in the frontward direction of the amputee with:
- a large amplitude right from the beginning of flexion of the prosthetic knee joint due to the additional link part moving in contact with the wide portion of the proximal part, of small dimension;
- a smaller amplitude up to the end of the flexion due to the additional link part moving in contact with the long portion of the proximal part, of larger dimension.

This advantage is obtained independently from the link part enabling the "braking effect". Such an oblong shape is able to provide the above-mentioned advantage whatever the mechanism used to achieve the "braking effect".

This being the case, an additional procured advantage is that, at the end of flexion, the link part can be tightly stretched, which results in hardening the "braking effect".

BRIEF DESCRIPTION OF THE DRAWINGS

Other features and advantages will become apparent from the detailed description of different embodiments of the invention, the description being accompanied by examples and reference to the appended drawings.

Identical parts or parts performing the same function will bear the same reference numerals for the different embodiments for the sake of simplification.

DETAILED DESCRIPTION OF THE EMBODIMENTS

Figures 1, 2:
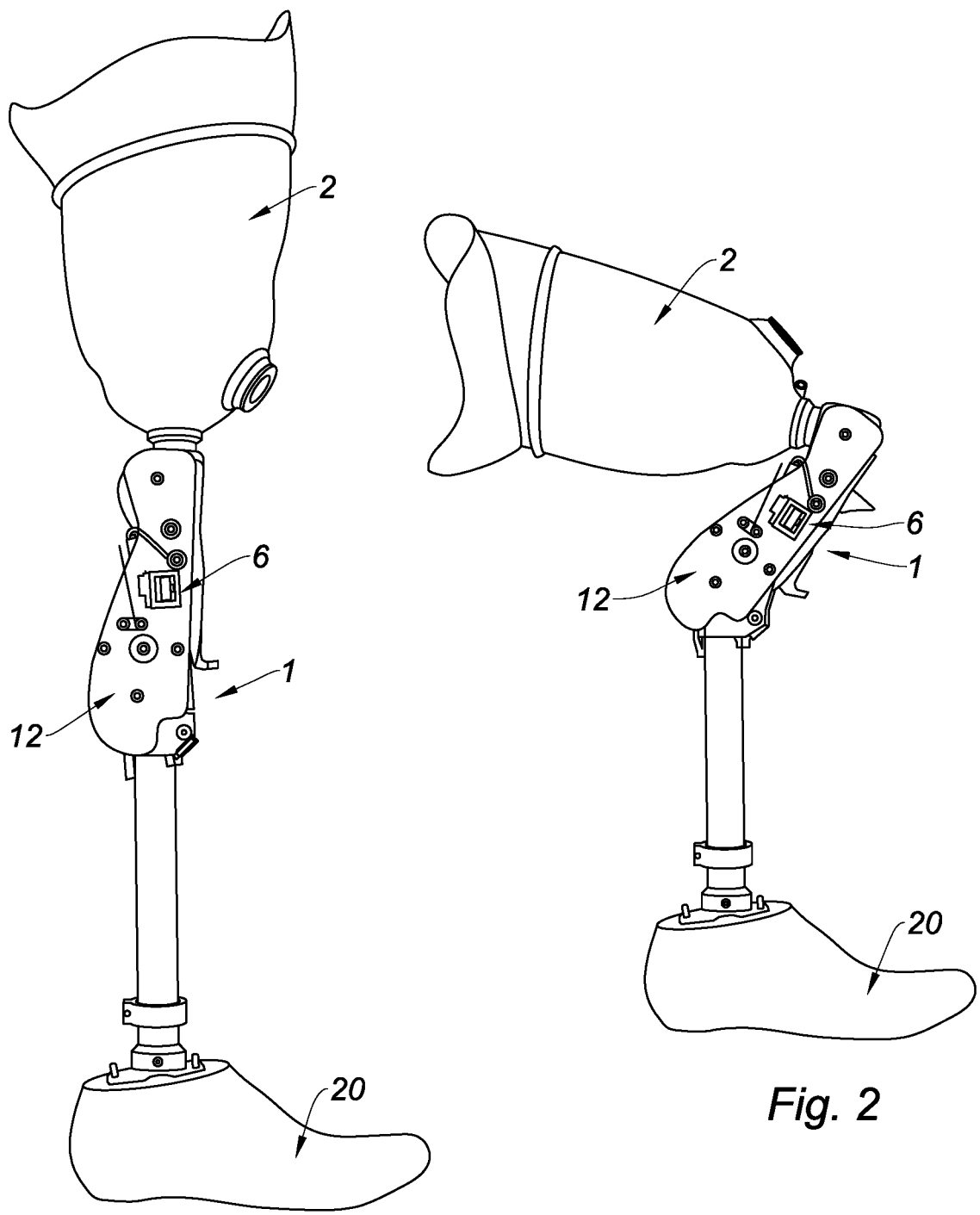
FIG. 1 is a side view of a prosthetic knee joint according to the invention, on which a prosthetic socket and a prosthetic foot are fitted, the prosthetic knee joint being in an extended position.
FIG. 2 is a similar view to FIG. 1 where the prosthetic knee joint is in a flexion position.
Figure 4:
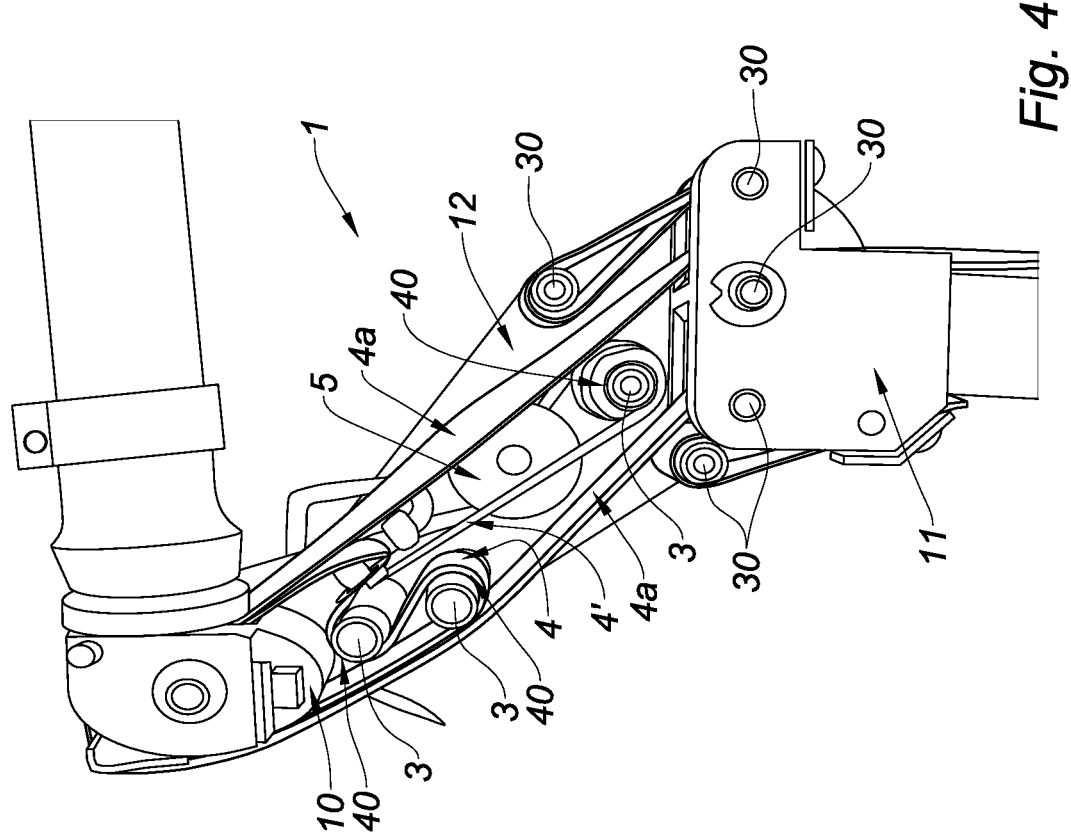
FIG. 4 is a similar view to FIG. 3, where the prosthetic knee joint is in a flexion position.
Figure 3:
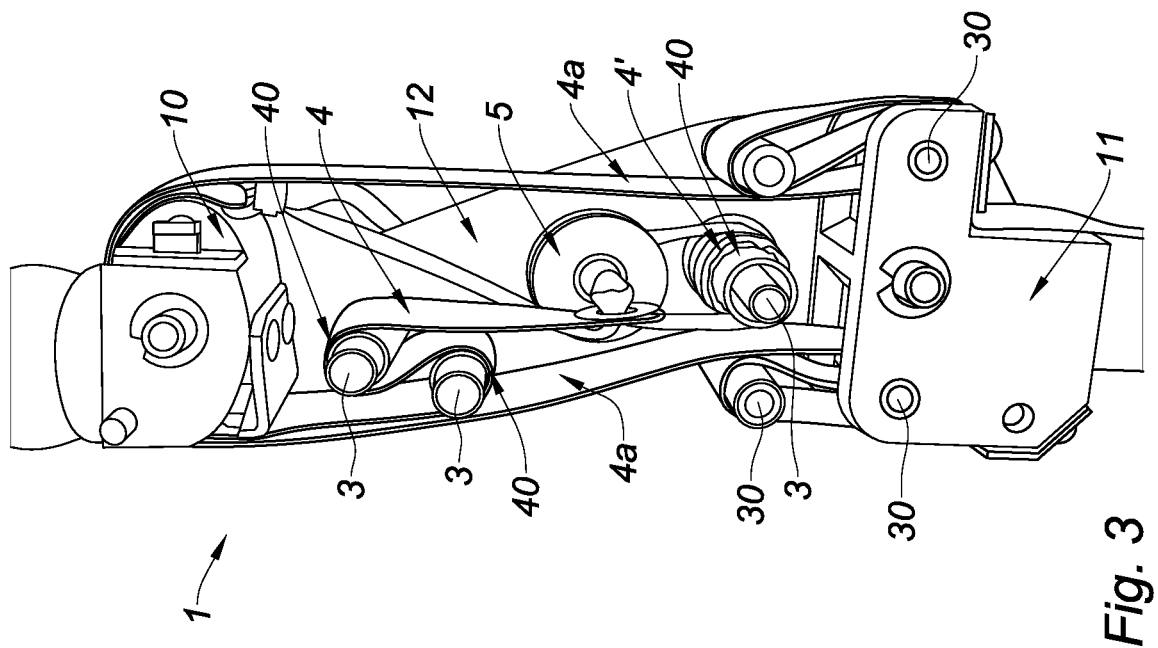
FIG. 3 is a side view of a prosthetic knee joint in the extended position, according to a first embodiment of the invention. One side is disassembled for better understanding.

The object of the invention is a prosthetic knee joint 1 for an above-the-knee amputee, comprising:
- a proximal part 10 designed to be connected to a prosthetic socket 2, the proximal part 10 being mobile in rotation around a first axis X'-X perpendicular to a sagittal plane of the amputee between an extended position and a flexion position of the prosthetic knee joint; the proximal part 10 being mobile in a first direction of rotation from the extended position to the flexion position, and mobile in an opposite second direction of rotation from the flexion position to the extended position;
- at least one part 3, the part 3 being fixed when the proximal part 10 is moved in the first direction of rotation;
- a link part 4, arranged to connect the proximal part 10 and the part 3, the link part 4 presenting a contact surface 40 with the part 3; the link part 4 and the part 3 being arranged so that, when the proximal part 10 is moved in the first direction of rotation, the link part 4 slides on the contact surface 40 being subjected to a first friction force.

Structure of the Prosthetic Knee Joint

The prosthetic knee joint 1 preferentially comprises two lateral edges 12 between which the proximal part 10 is fitted. The lateral edges 12 can be made in the form of plates. The lateral edges 12 can be metal sides, for example made from aluminium. The lateral edges 12 can also be made from carbon. The lateral edges 12 preferentially extend in a sagittal plane of the amputee.

Link Part

The link part 4 is preferentially flexible. The link part 4 is advantageously selected from the group comprising a strap, a cord, or a belt. The link part 4 advantageously comprises a part wound around the part 3. The part of the link part 4 wound around the part 3 is preferably a cord 4'. As illustrated in FIGS. 3 to 6, the link part 4 can be a strap extended by the cord 4'. The cord 4' enables the volume to be reduced significantly as compared with a strap. The link part 4 advantageously has a high tensile strength and wear resistance. When the link part 4 is a strap, the latter is for example made from Cordura®. The link part 4 can be guided by means of a guide plate.

Figure 7:
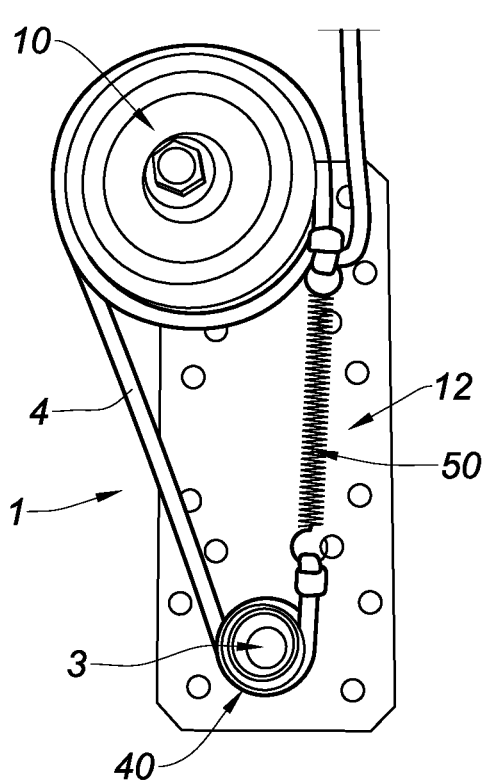
FIG. 7 is a schematic side view of a prosthetic knee joint according to a second embodiment.
Figure 8:
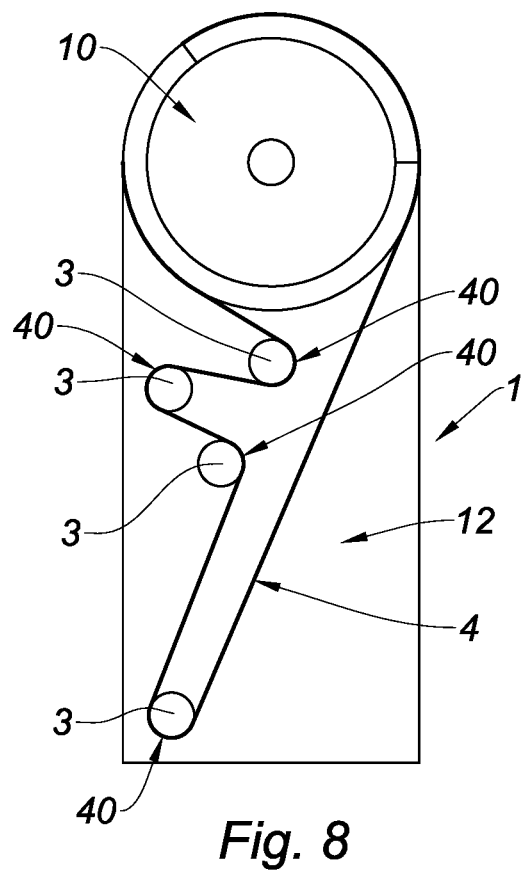
FIG. 8 is a schematic view in sagittal cross-section of a prosthetic knee joint according to a third embodiment.

The Part(s) that are Fixed when the Proximal Part is Moved in the First Direction of rotation As illustrated in FIG. 7, the prosthetic knee joint 1 can comprise a single part 3, the single part 3 being fixed when the proximal part 10 is moved in the first direction of rotation. More precisely, the single part 3 can be fixed to a lateral edge 12 of the prosthetic knee joint 1. The link part 4 can be a cord 4' wound around the proximal part 10 and around the single part 3, preferably over several winds. The single part 3 is preferably tubular-shaped. The single part 3 can be made from metal or a metal alloy such as steel.

As illustrated in FIGS. 3 to 6, 8 and 11-12, the prosthetic knee joint 1 can comprise a set of parts 3, the parts 3 of the set being fixed when the proximal part 10 is moved in the first direction of rotation. More precisely, the parts 3 of the set can each comprise a fixed portion when the proximal part 10 is moved in the first direction of rotation. The fixed portion is preferentially secured to a lateral edge 12 of the prosthetic knee joint 1. The link part 4 is arranged to connect the proximal part 10 and set of parts 3. The link part 4 presents contact surfaces 40 with the set of parts 3. Each part 3 of the set is preferentially tubular-shaped. More precisely, the fixed portion of the parts 3 of the set is preferentially tubular-shaped. Each part 3 of the set can be made from metal or a metal alloy such as steel.

Cooperation between the Link Part and the Part or Parts

As illustrated in FIG. 7, in the case of a single part 3, the link part 4 and part 3 are advantageously arranged so that, when the proximal part 10 is moved in the second direction of rotation, the link part 4 slides on the contact surface 40 being subjected to a second friction force strictly lower than the first friction force. The first and second friction forces, respectively noted $f_1$ and $f_2$, advantageously present a ratio $f_1/f_2$ higher than or equal to 10. To do this, for example purposes, a spring 50 is arranged to connect two ends of the link part 4. The second friction force $f_2$ is strictly lower than the first friction force $f_1$ as the spring 50 is arranged to exert a tension only in the first direction of rotation. The ratio $f_1/f_2$ depends on the stiffness of the spring 50 which conditions the tension, and thereby slowing-down of the flexion of the prosthetic knee joint 1.

The spring 50 can be replaced by a shock absorber the role of which is to prevent a too rapid flexion of the prosthetic knee joint 1. The spring 50 can also be associated with such a shock absorber.

According to an alternative, the single part 3 is advantageously mobile when the proximal part 10 is moved in the second direction of rotation. The ratio $f_1/f_2$ then becomes much higher than 10. The second friction force $f_2$ can then be almost zero if the single part 3 operates in similar manner to a freewheel.

As illustrated in FIGS. 3 to 6, 8, and 11-12, in the case of a set of parts 3, the link part 4 and the set of parts 3 are arranged so that, when the proximal part 10 is moved in the first direction of rotation, the link part 4 slides on each contact surface 40 being subjected to the corresponding first friction force. The link part 4 and the set of parts 3 are advantageously arranged so that the link part 4 forms strings around the set of parts 3. At least one part 3 of the set advantageously presents a mobile portion when the proximal part 10 is moved in the second direction of rotation. To do this, a freewheel bearing 31, forming the mobile portion, can be fitted on the fixed portion of the part 3. Such a freewheel bearing 31 significantly reduces the friction forces to which the link part 4 is subjected when the proximal part 10 is moved in the second direction of rotation. In the embodiments where the link part 4 comprises a cord 4', the cord 4' is advantageously wound around the portion mobile of the part 3.

According to a particular embodiment, the speed of rotation of at least one of the parts 3 can be controlled by a motor (not shown) so as to help the amputee to stand up when he wants to. The motor can be actuated directly by the amputee, or actuated by a force sensor as soon as the measured force exceeds a threshold translating the amputee's desire to stand up.

Bias in Extended Position

Figure 12:
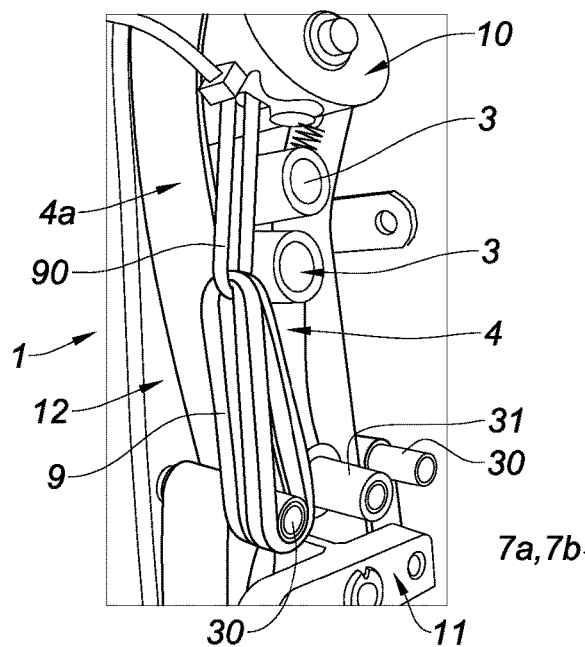
FIG. 12 is a partial view of a prosthetic knee joint according to the invention, illustrating flexible biasing means to bias the proximal part to the extended position.

The prosthetic knee joint 1 advantageously comprises flexible bias means to bias the proximal part 10 to the extended position. For example purposes as illustrated in FIG. 12, the flexible bias means comprise an elastic band 9 fitted on a tie flange 90, the tie flange 90 being secured to the proximal part 10. As a variant, the flexible bias means can comprise a cable and a spring. The flexible bias means are optional, in particular when a rotary tensioner 5 and a freewheel bearing 31 fitted on a part 3 are used, biasing to the extended position being able to be performed by simple gravity due to the ratio $f_1/f_2$ higher than or equal to 10, or even much higher than 10.

Tensioning of the Link Part and Modulation of the Mechanical Tension

The prosthetic knee joint 1 advantageously comprises tensioning means arranged to exert a mechanical tension on the link part 4. In the embodiments where the link part 4 comprises a cord 4', the tensioning means are advantageously arranged to exert a mechanical tension on the cord 4'.

As illustrated in FIG. 7 and set out previously, the tensioning means can comprise a spring 50 connecting two ends of the link part 4.

As illustrated in FIGS. 3 to 6, the tensioning means advantageously comprise a rotary tensioner 5. According to an alternative, the tensioning means can comprise a clamp surrounding the link part 4 so as to clamp the latter.

Figure 9A:
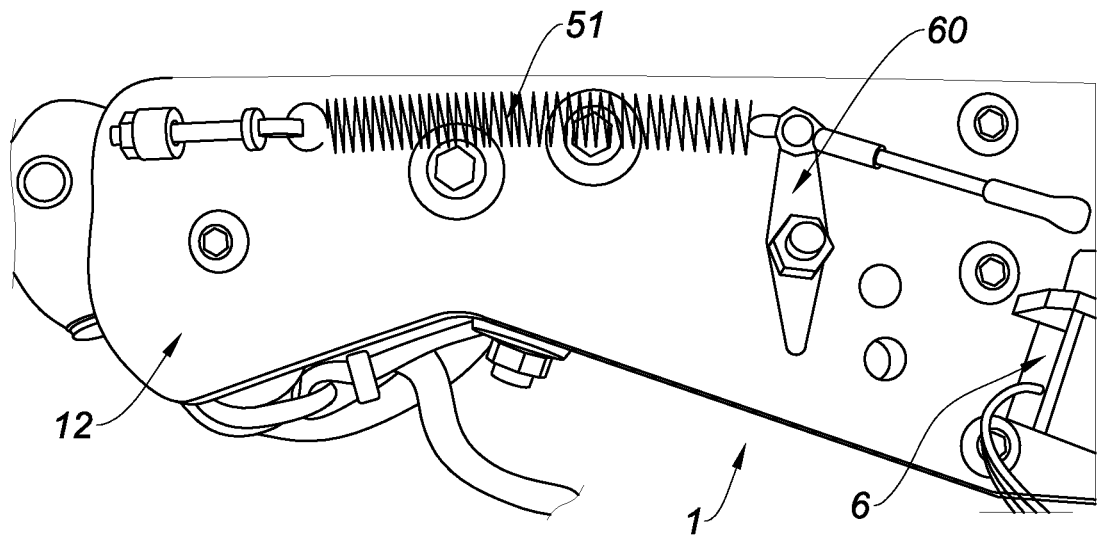
FIG. 9a is a side view on an enlarged scale of a prosthetic knee joint according to the invention illustrating an embodiment of the control of the tensioning means.
Figure 9B:
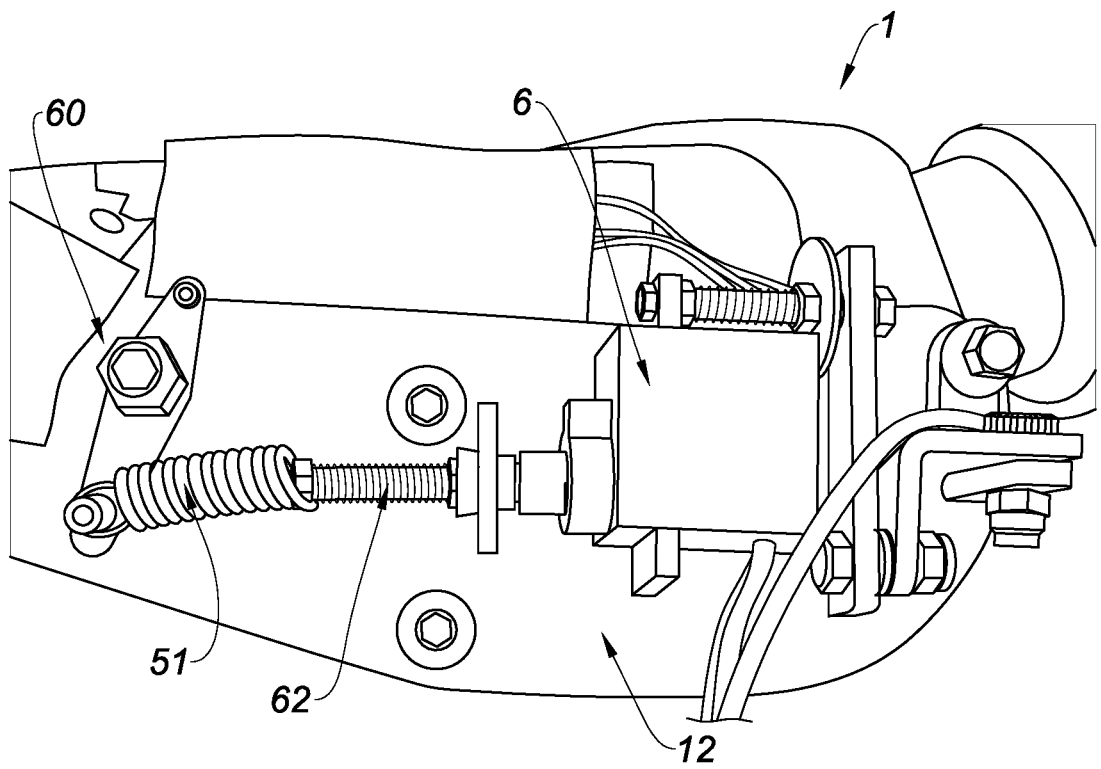
FIG. 9b is a similar view to FIG. 9a illustrating another embodiment of the control.

The prosthetic knee joint 1 advantageously comprises control means configured to control the tensioning means. The control means can be arranged on a surface of a lateral edge 12 of the prosthetic knee joint 1. As illustrated in FIGS. 9a and 9b, the control means advantageously comprise a servomotor 6 configured to modify a torque exerted on the rotary tensioner 5, i.e. to increase or reduce the torque. To do this, the servomotor 6 is configured to actuate a plate 60 exerting a torque on the rotary tensioner 5. The servomotor 6 can actuate the plate 60 via a flexible connecting rod. According to a variant illustrated in FIG. 9b, the servomotor 6 can actuate the plate 60 by modifying the tension of a spring 51. To do this, the servomotor 6 can comprise an endless screw 62 fitted on one end of the spring 51. The other end of the spring 51 is fitted on the plate 60. The endless screw 62 enables the force of the servomotor 6 to be reduced when the latter stretches the spring 51.

As illustrated in FIG. 9a, the tensioning means can also be controlled manually by means of the plate 60 arranged on a surface of a lateral edge 12. The amputee is thus able to release the prosthetic knee joint 1 in case of failure of the is servomotor 6.

The prosthetic knee joint 1 advantageously comprises a stress gauge arranged to measure the torque exerted on the rotary tensioner 5. The stress gauge is preferentially fixed to the servomotor 6.

Figure 11:
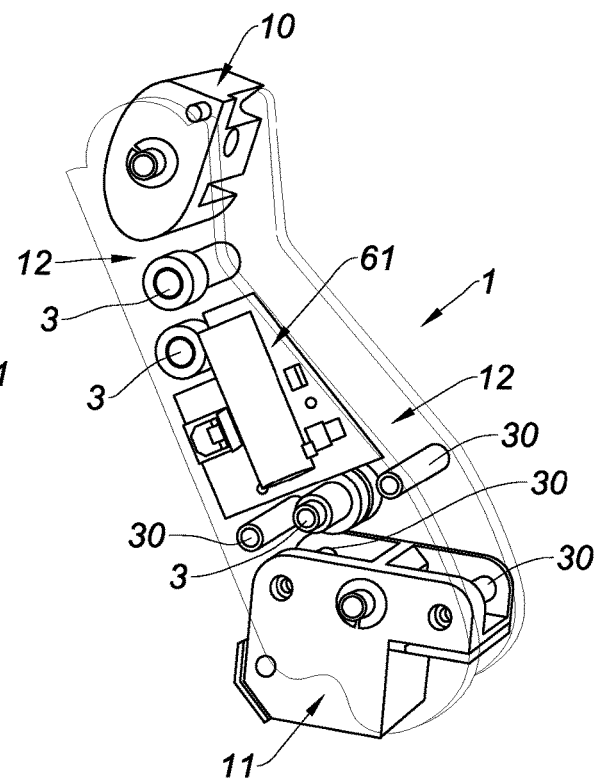
FIG. 11 is a schematic side view of a prosthetic knee joint according to the invention (in the absence of a link part), equipped with a printed circuit board.

As illustrated in FIG. 11, the prosthetic knee joint 1 advantageously comprises a printed circuit board 61. The printed circuit board 61 is preferentially located between the two lateral edges 12. The servomotor 6 is advantageously electrically connected to the printed circuit board 61.

Figure 13:
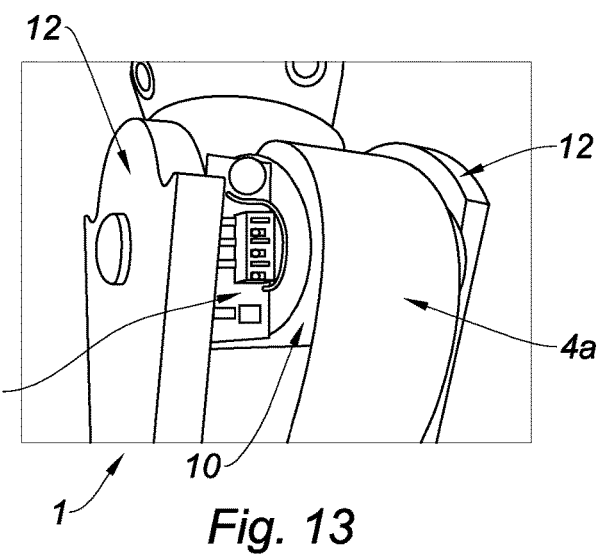
FIG. 13 is a partial view of a prosthetic knee joint according to the invention, illustrating means for measuring a pivoting angle between the extended position and the flexion position in a sagittal plane of the amputee.

The proximal part 10 presents a pivoting angle between the extended position and the flexion position in a sagittal plane of the amputee. The prosthetic knee joint 1 advantageously comprises measuring means arranged to measure the pivoting angle. As illustrated in FIG. 13, the measuring means preferably comprising an accelerometer 7*a* and a gyrometer 7*b* fitted on the proximal part 10. The accelerometer 7*a* and gyrometer 7*b* are electrically connected to the printed circuit board 61, for example by a flexible electric braid. The servomotor 6 can thus modulate the mechanical tension exerted on the link part 4 by the tensioning means according to the measured pivoting angle and the speed at which it varies.

According to a variant, the measuring means can comprise a potentiometric sensor, preferably of resistive strip type. One advantage procured by a resistive strip is to avoid the presence of a flexible electric braid (connecting the accelerometer 7*a* and gyrometer 7*b* to the printed circuit board 61) in the vicinity of the proximal part 10. The electric braid is in fact liable to degrade (or even break) in contact with the proximal part 10 after a multitude of flexions of the prosthetic knee joint 1. The potentiometric sensor can be fitted on a part 3 close to the proximal part 10. For example purposes, the measuring means can comprise a spring-mounted stud connected to the proximal part 10 so as to slide on the resistive strip. The resistive strip can be stuck onto the part 3 near the proximal part 10.

Anticipation of the Beginning of Flexion of the Prosthetic Knee Joint

Figure 10:
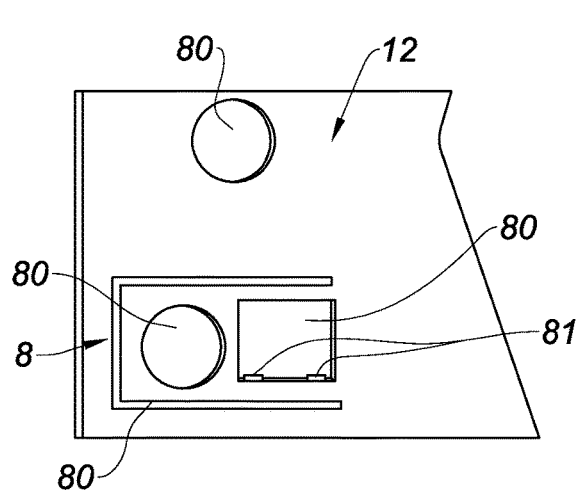
FIG. 10 is a schematic view of a force sensor with resistive gauges equipping a prosthetic knee joint according to the invention.

The prosthetic knee joint 1 advantageously comprises a force sensor 8 arranged to measure the force exerted by the link part 4 on the part 3 or a part 3 included in the set of parts 3. As illustrated in FIG. 10, the force sensor 8 is preferentially arranged on a lateral edge 12 of the prosthetic knee joint 1. The lateral edge 12 preferentially comprises openings 80 arranged therein. The force sensor 8 preferentially comprises a plurality of electric resistances 81 fixed to said lateral edge 12, for example by sticking, inside the openings 80. The electric resistances 81 are preferentially cabled as a Wheatstone bridge. When the part 3 presents the form of a tube, the force sensor 8 can be arranged at one end of the tube which twists when the flexion of the prosthetic knee joint 1 takes place.

The prosthetic knee joint 1 advantageously comprises warning means configured to warn the amputee as soon as the force measured by the force sensor 8 exceeds a threshold. The warning means preferably comprise a vibrator. The vibrator is electrically connected to the printed circuit board 61, for example by a flexible electric braid. The vibrator is preferentially arranged inside the proximal part 10 so that the amputee can feel it better. Nevertheless, the vibrator can also be fitted on a flank 12 close to the proximal part 10 in order to avoid degradation of the flexible electric braid.

The prosthetic knee joint 1 can also comprise a flexion aid device configured to help the elderly amputee to sit down. This device can for example be associated with the force sensor 8 to help the amputee as soon as the measured force exceeds a certain threshold. As an alternative, the device can be directly controlled by the amputee.

Prosthetic Knee Joint with Polyaxial Articulation

The prosthetic knee joint 1 advantageously comprises:
a distal part 11, designed to be connected to a prosthetic foot 20, the distal part 11 being mobile in rotation around a second axis Y'-Y perpendicular to a sagittal plane of the amputee between a forward movement position and a backward movement position of the prosthetic foot 20; the distal part 11 being mobile in a first direction of rotation from the forward movement position to the backward movement position;
an additional link part 4*a* arranged to connect the proximal part 10 and the distal part 11 so that, when the proximal part 10 is moved in the first direction of rotation, the distal part 11 is moved in the first direction of rotation.

Figure 5:
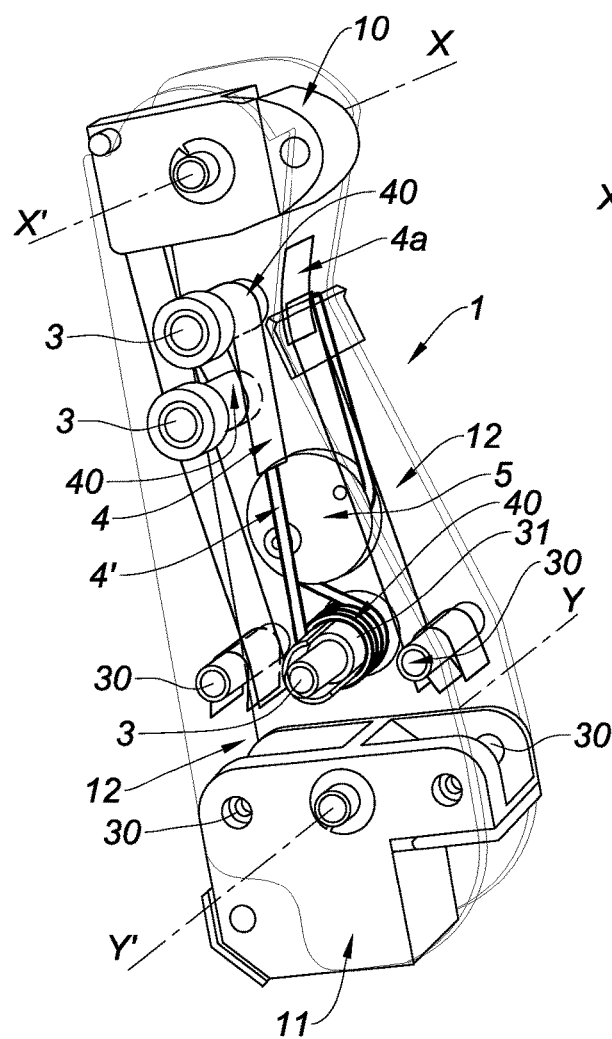
FIG. 5 is a schematic perspective view of a prosthetic knee joint in the extended position, according to the first embodiment of the invention.
Figure 6:
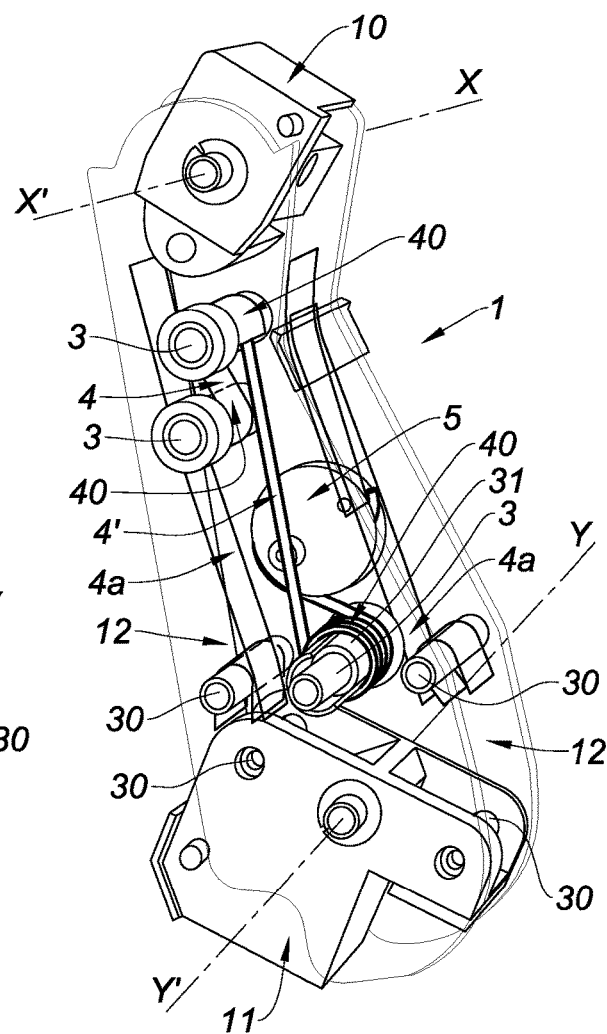
FIG. 6 is a similar view to FIG. 5, where the prosthetic knee joint is in a flexion position.

The second axis Y'-Y is parallel to the first axis X'-X (FIGS. 5 and 6 are misleading on account of the vanishing point).

The proximal part 10 advantageously presents an oblong shape in a sagittal plane of the amputee. In other words, the proximal part 10 presents a portion that is longer than it is wide in a sagittal plane of the amputee. As a reminder, one advantage procured by an oblong shape is to obtain a movement of the proximal part 10 towards the front of the amputee with:
a large amplitude right from the beginning of flexion of the prosthetic knee joint 1 on account of the additional link part 4*a* moving in contact with the wide portion of the proximal part 10, of small dimension;
a smaller amplitude up to the end of the flexion due to the additional link part 4*a* moving in contact with the long portion of the proximal part 10, of larger dimension.

Furthermore, at the end of flexion, the link part 4, 4' can be tightly stretched, which results in hardening the "braking effect".

The dimensions of the long portion and of the wide portion of the proximal part 10 can thus be determined:
according to the required amplitude at the beginning of flexion of the movement of the proximal part 10 towards the front of the amputee, and
according to the required tension of the link part 4 at the end of flexion.

The proximal part 10 preferably presents the shape of an ellipsoid or an ovoid.

For additional safety during walking when placing the heel (for a version without electronics for example), the additional link part 4*a* and set of parts 3 are advantageously arranged so that the additional link part 4*a* forms strings around the set of parts 3. The additional link part 4*a* is advantageously selected from the group comprising a strap, a cord, or a belt. The additional link part 4*a* advantageously has a high tensile strength and wear resistance. When the additional link part 4*a* is a strap, the latter is for example made from Cordura®.

The proximal part 10 and distal part 11 present speeds of rotation in the first direction of rotation respectively noted $Vp_1$ and $Vd_1$. The prosthetic knee joint 1 advantageously comprises means 30 designed to receive the additional link part 4*a*, the means 30 being configured so that $Vd_1$ is strictly lower than $Vp_1$ with preferably $Vp_1/Vd_1 \geq 3$. The means 30 advantageously form pulleys configured in the form of a reeving system so as to obtain the required ratio $Vp_1/Vd_1$. The means 30 are mounted free in rotation. The means 30 preferentially tubular-shaped. At least one freewheel bearing 31 can be fitted on the means 30 so as to generate a braking effect on flexion of the prosthetic knee joint 1 via the additional link part 4*a*.

The invention is not limited to the described embodiments. The person skilled in the trade is able to consider their technically operative combinations and to substitute equivalences for the latter.

The invention claimed is:

1. Prosthetic knee joint for an above-the-knee amputee, the joint comprising:
a proximal part designed to be connected to a prosthetic socket, the proximal part being adapted to be mobile in rotation around a first axis perpendicular to a sagittal plane of the amputee between an extended position and a flexion position of the prosthetic knee joint, the proximal part being mobile in a first direction of rotation from the extended position to the flexion position, and mobile in an opposite second direction of rotation from the flexion position to the extended position;

at least one part that is fixed when the proximal part moves in the first direction of rotation;

a link part, arranged to connect the proximal part and the at least one part, the link part contacting the at least one part;

wherein the link part and the at least one part are arranged so that, when the proximal part moves in the first direction of rotation from a set position, the link part slides on the at least one part and is subjected to a first friction force, and when the proximal part moves in the second direction of rotation from the set position, the link part slides on the at least one part and is subjected to a second friction force strictly lower than the first friction force.

2. Prosthetic knee joint according to claim 1, wherein the first and second friction forces, respectively noted $f_1$ and $f_2$, present a ratio $f_1/f_2$ higher than or equal to 10.

3. Prosthetic knee joint according to claim 1, wherein the at least one part is mobile when the proximal part moves in the second direction of rotation.

4. Prosthetic knee joint according to claim 1, comprising tensioning means arranged to exert a mechanical tension on the link part.

5. Prosthetic knee joint according to claim 4, comprising control means configured to control the tensioning means.

6. Prosthetic knee joint according to claim 5, wherein the tensioning means comprise a rotary tensioner, and the control means comprise a servomotor configured to modify a torque exerted on the rotary tensioner.

7. Prosthetic knee joint according to claim 6, comprising a stress gauge arranged to measure the torque exerted on the rotary tensioner.

8. Prosthetic knee joint according to claim 1, wherein the proximal part is adapted to present a pivoting angle between the extended position and the flexion position in the sagittal plane of the amputee, the prosthetic knee joint comprising a device arranged to measure the pivoting angle, the device being selected from the group consisting of a potentiometer, a resistive strip, an accelerometer, and a gyroscope.

9. Prosthetic knee joint according to claim 1, comprising a force sensor arranged to measure the force exerted by the link part on the at least one part.

10. Prosthetic knee joint according to claim 9, comprising a warning device configured to warn the amputee as soon as the force measured by the force sensor exceeds a threshold.

11. Prosthetic knee joint according to claim 1, comprising flexible biasing means arranged to bias the proximal part to the extended position.

12. Prosthetic knee joint according to claim 1, wherein the link part is a strap, a cord, or a belt.

13. Prosthetic knee joint according to claim 1, wherein the link part forms a complete winding around the at least one part.

14. Prosthetic knee joint according to claim 1, comprising additional parts that are fixed when the proximal part is moved in the first direction of rotation from the extended position to the flexion position, the link part being arranged to connect the proximal part and the additional parts, the link part sliding on the additional parts, and the link part and the additional parts being arranged so that, when the proximal part is moved in the first direction of rotation, the link part slides on the additional parts and is subjected to the corresponding first friction force.

15. Prosthetic knee joint according to claim 14, wherein the link part and the additional parts are arranged so that the link part forms a zig-zag around the additional parts.

16. Prosthetic knee joint according to claim 1, comprising:

a distal part, designed to be connected to a prosthetic foot, the distal part being adapted to be mobile in rotation around a second axis perpendicular to the sagittal plane of the amputee between an anterior position representative of the extended position and a posterior position of the prosthetic foot representative of the flexion position, the distal part being mobile in a first direction of rotation from the anterior position to the posterior position; and an additional link part arranged to connect the proximal part and the distal part so that, when the proximal part is moved in the first direction of rotation, the distal part is moved from the anterior position to the posterior position.

17. Prosthetic knee joint according to claim 16, wherein the link part, the at least one part, and additional parts are arranged so that the link part forms strings around the additional parts, and the additional link part and the additional parts are arranged so that the additional link part forms strings around the additional parts.

18. Prosthetic knee joint according to claim 16, wherein the additional link part is a strap, a cord, or a belt.

19. Prosthetic knee joint according to claim 17, wherein the additional link part is a strap, a cord, or a belt.

20. Prosthetic knee joint according to claim 16, wherein a movement of the proximal part with a first speed of rotation noted $Vp_1$ causes a movement of the distal part with a second speed noted $Vd_1$; the prosthetic knee joint comprising a support designed to receive the additional link part, the support being configured so that $Vd_1$ is strictly lower than $Vp_1$.

21. Prosthetic knee joint according to claim 1, wherein the proximal part is adapted to present an oblong shape in the sagittal plane of the amputee.

22. Prosthetic knee joint according to claim 20, wherein the support is configured so that $Vp_1/Vd_1 \geq 3$.

23. Prosthetic knee joint according to claim 10, wherein the warning device comprises a vibrator.

24. Prosthetic knee joint according to claim 13, wherein the complete winding is formed by a cord.

25. Prosthetic knee joint according to claim 1, wherein the at least one part comprises a freewheel bearing that is configured such that the second friction force is lower than the first friction force.

* * * * *